United States Patent [19]

Kleuser et al.

[11] 4,305,750

[45] Dec. 15, 1981

[54] HERBICIDES BASED ON PYRIDAZONES

[75] Inventors: Dieter Kleuser, Frankenthal; August Wigger, Neuhofen, both of Fed. Rep. of Germany

[73] Assignee: BASF Aktiengesellschaft, Fed. Rep. of Germany

[21] Appl. No.: 125,281

[22] Filed: Feb. 27, 1980

[30] Foreign Application Priority Data

Mar. 8, 1979 [DE] Fed. Rep. of Germany ....... 2909158

[51] Int. Cl.$^3$ ............................................. A01N 25/22
[52] U.S. Cl. .................................. 71/92; 71/DIG. 1; 71/100; 71/118; 71/121
[58] Field of Search ............................. 71/92, DIG. 1

[56] References Cited

U.S. PATENT DOCUMENTS

| | | | |
|---|---|---|---|
| 3,210,353 | 10/1965 | Reicheneder et al. | 71/92 |
| 3,330,821 | 7/1967 | Harman et al. | 260/239 |
| 3,937,730 | 2/1976 | Vogel et al. | 260/562 B |

FOREIGN PATENT DOCUMENTS 2547968 4/1977 Fed. Rep. of Germany.
1389479 4/1975 United Kingdom.
1554595 10/1979 United Kingdom.

*Primary Examiner*—Catherine L. Mills
*Attorney, Agent, or Firm*—Keil & Witherspoon

[57] ABSTRACT

Herbicides based on an aqueous suspension of from 20 to 50 percent by weight of 1-phenyl-4-amino-5-chloropyridaz-6-one or 1-phenyl-4-amino-5-bromo-pyridaz-6-one, from 2 to 10 percent by weight of dispersant, from 0.5 to 5 percent by weight of silica and from 0.5 to 5 percent by weight of a block polymer of propylene glycol, propylene oxide and ethylene oxide, which additionally contain a thiolcarbamate, a chloroacetanilide or a 2,6-dinitroaniline, the weight ratio of pyridazone to thiolcarbamate, chloroacetanilide or 2,6-dinitroaniline being from 4:1 to 1:2, a process for their preparation, and their use for combating undesired plant growth.

5 Claims, No Drawings

HERBICIDES BASED ON PYRIDAZONES

The present invention relates to herbicides in the form of stable aqueous suspensions which contain a mixture of active ingredients comprising 1-phenyl-4-amino-5-chloro-pyridaz-6-one or 1-phenyl-4-amino-5-bromo-pyridaz-6-one and a thiolcarbamate or a chloroacetanilide or a 2,6-dinitroaniline.

It is known that 1-phenyl-4-amino-5-chloro-pyridaz-6-one, 1-phenyl-4-amino-5-bromo-pyridaz-6-one, thiolcarbamates, chloroacetanilides and 2,6-dinitroanilines are herbicidally active (German Pat. No. 1,105,232, U.S. Pat. Nos. 3,330,821 and 3,185,720 and German Laid-Open Applications DOS No. 2,328,340 and DOS No. 2,241,408).

Furthermore, it is known that a herbicide, in the form of a stable aqueous suspension, is obtained if from 20 to 50 percent by weight of 1-phenyl-4-amino-5-chloro-pyridaz-6-one or 1-phenyl-4-amino-5-bromo-pyridaz-6-one are finely milled with water, from 2 to 10 percent by weight of a dispersant, from 0.5 to 5 percent by weight of silica and from 0.5 to 5 percent by weight of a block polymer of propylene glycol, propylene oxide and ethylene oxide (German Laid-Open Application DOS No. 2,547,968).

If, in order to achieve a broader spectrum of action, mixtures of herbicidally active ingredients, for example of pyridazones and thiolcarbamates, chloroacetanilides or 2,6-dinitroanilines, are to be applied, either a tank mixture or a finished formulation may be employed.

A tank mixture is an aqueous dilution, brought to a particular use concentration, of the two formulations of the individual active ingredients, which may be in the form of an emulsion concentrate, a suspension concentrate (flowable) or a wettable powder. With such tank mixtures, the miscibility of the formulations employed often presents difficulties. Just as the chemical and physical properties of the active ingredient determine the type of formulation, so does the latter determine the choice of solvents and assistants, such as emulsifiers, dispersants and wetting agents. Where two different types of formulation are involved, and even where similar types of formulation are involved, incompatibility in the tank mixture may be encountered. The consequences of such incompatibility are, inter alia, creaming, coagulation or aggregation, which make it impossible to apply the mixture.

A finished formulation, on the other hand, is a formulation containing at least two active ingredients which are present conjointly, as an emulsion concentrate, a suspension concentrate (flowable) or a wettable powder. These formulations can be directly converted to spray liquors of the appropriate use concentration by diluting them with water. In principle, all types of active ingredients can be combined in this way. However, formulating two or more active ingredients in one type of formulation is in practice substantially affected, or even made impossible, by differences in, for example, the solubilities, melting points, specific gravities and stability of the active ingredients. A further difficulty resides in finding a suitable single system of assistants, eg. emulsifiers, wetting agents or dispersants, for the active ingredients to be employed. This applies particularly to mixtures of solid and liquid active ingredients.

We have found that herbicides based on an aqueous suspension containing from 20 to 50 percent by weight of 1-phenyl-4-amino-5-chloro-pyridaz-6-one or 1-phenyl-4-amino-5-bromo-pyridaz-6-one, from 2 to 10 percent by weight of dispersant, from 0.5 to 5 percent by weight of silica and from 0.5 to 5 percent by weight of a block polymer of propylene glycol, propylene oxide and ethylene oxide, which additionally contain a thiolcarbamate of the formula I

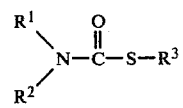

where
R$^1$ is alkyl of up to 4 carbon atoms,
R$^2$ is alkyl of up to 4 carbon atoms or cyclohexyl and
R$^3$ is alkyl of up to 4 carbon atoms, 2,3-dichloroallyl or 2,3,3-trichloroallyl, or a chloroacetanilide of the formula II

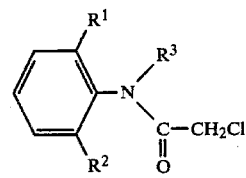

where
R$^1$ and R$^2$ are methyl or ethyl and
R$^3$ is alkyl of up to 3 carbon atoms or alkoxyalkyl of up to 4 carbon atoms,
or a 2,6-dinitroaniline of the formula III

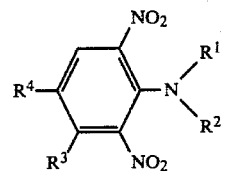

where
R$^1$ is hydrogen or alkyl of up to 5 carbon atoms,
R$^2$ is alkyl of up to 5 carbon atoms and
R$^3$ and R$^4$ are unsubstituted or halogen-substituted alkyl of up to 2 carbon atoms,
the weight ratio of pyridazone to thiolcarbamate, chloroacetanilide or dinitroaniline being from 4:1 to 1:2, constitute a stable formulation.

It was in no way to be expected that on adding the thiolcarbamates, the chloroacetanilides or the 2,6-dinitroanilines of the formulae I, II or III to the aqueous suspension concentrate, which contains the pyridazone, a stable formulation would be obtained without further addition of assistants, such as emulsifiers or wetting agents, since it is known that water-insoluble substances of the said categories of active ingredients do not form stable dispersions or emulsions with water.

It is particularly surprising that on diluting the concentrated formulations according to the invention with water to the use concentration, ie. diluting from 5 to 10 liters of the formulation with from 50 to 600 liters of water, stable spray liquors also result. Such stable liquors can, for example, not be prepared if a thiolcarbamate, a chloroacetanilide or a 2,6-dinitroaniline of the formula I, II or III respectively is added, in the above weight ratio of active ingredients, to a dilute spray liquor comprising 6 liters of a formulation according to Example 1 of German Laid-Open Application DOS No. 2,547,968 and from 50 to 600 liters of water. In this case, the added water-insoluble compound separates out immediately. Only the thorough incorporation of the thiolcarbamate, the chloroacetanilide or the dinitroaniline into a formulation according to Example 1 of German Laid-Open Application DOS No. 2,547,968 gives a stable concentrated multi-phase system which even on further dilution to the use concentration with water remains stable and from which the added thiolcarbamate, chloroacetanilide or dinitroaniline does not separate out.

Examples of suitable herbicidal thiolcarbamates of the formula I are 2,3-dichloroallyl N,N-diisopropylthiolcarbamate, 2,3,3-trichloroallyl N,N-diisopropylthiolcarbamate, ethyl N-ethyl-N-cyclohexyl-thiolcarbamate and ethyl N-N-di-n-propyl-thiolcarbamate. Examples of suitable chloroacetanilides of the formula II are 2-ethyl-6-methyl-N-(1-methyl-2-methoxyethyl)-chloroacetanilide and 2,6-diethyl-N-methoxymethyl-chloroacetanilide and examples of suitable 2,6-dinitroanilines of the formula III are 2,6-dinitro-3,4-dimethyl-N-(1-ethyl-n-propyl)-aniline and 2,6-dinitro-4-trifluoromethyl-N,N-di-n-propylaniline.

To prepare the herbicides according to the invention, an aqueous suspension which contains from 20 to 50 percent by weight of 1-phenyl-4-amino-5-chloropyridaz-6-one or 1-phenyl-4-amino-5-bromo-pyridaz-6-one, from 2 to 10 percent by weight of dispersant, from 0.5 to 5 percent by weight of silica and from 0.5 to 5 percent by weight of a block polymer of propylene glycol, propylene oxide and ethylene oxide is first prepared by milling in a mill, for example a sand mill or a bead mill. The second herbicidal active ingredient is added to this suspension concentrate, with vigorous stirring, and a stable formulation is thereby obtained. The amount of the second herbicidal active ingredient is selected so that the weight ratio of pyridazone to thiolcarbamate or chloroacetanilide or 2,6-dinitroaniline is from 4:1 to 1:2.

The dispersants used may be any surfactants conventionally employed as assistants in the formulation of crop protection agents. The preferred dispersant is the sodium salt of a condensate of phenolsulfonic acid, urea and formaldehyde. Such condensates are described, for example, in German Pat. No. 1,113,457 and German Pat. No. 1,178,081.

For the purposes of the invention, the block polymer is a product formed by reacting propylene glycol first with propylene oxide and then with ethylene oxide. A preferred product has a polypropylene oxide core of molecular weight from 3,000 to 3,500, and contains 50% of ethylene oxide units, so that its total molecular weight is from about 6,000 to 7,000.

The silica used is preferably synthetic silica, ie. silica prepared by chemical precipitation. The water used is preferably completely demineralized.

In addition to the pyridazone, dispersant, block polymer and silica the suspension concentrate, which serves as the basis for the preparation of the herbicides according to the invention, may contain from 5 to 15 percent by weight of antifreeze. Examples of suitable materials are ethylene glycol, propylene glycol, glycerol and urea, ethylene glycol being preferred.

If the thiolcarbamate or chloroacetanilide or dinitroaniline are solid under normal conditions, it is advisable to dissolve them in an alkylbenzene before adding them to the mixture, so as to ensure the stability of the formulation at relatively low temperatures. An amount of from 10 to 50 ml of solvent per liter of formulation, ie. from 1 to 5% by volume of solvent is sufficient.

Suitable alkylbenzenes are xylenes, isopropylbenzene, 1,2,3,4-tetramethylbenzene, butylbenzenes and pentylbenzenes. Mixtures of these solvents may also be used.

The Examples which follow illustrate the method of preparation and show the advantageous properties of the herbicides according to the invention.

EXAMPLE 1

(a) 430 g of 1-phenyl-4-amino-5-chloropyridaz-6-one, 100 g of ethylene glycol, 60 g of the sodium salt of a condensate of phenolsulfonic acid, urea and formaldehyde, 20 g of synthetic silica and 30 g of a block polymer consisting of a polypropylene oxide core of molecular weight about 3,250, onto which ethylene oxide has been grafted until the molecular weight reaches about 6,500, are mixed and made up to 1,000 ml with water.

This mixture is milled in a bead mill until about 95 percent by weight of the particles are smaller than $2\mu$.

220 g of 2,3-dichloroallyl N,N-diisopropyl-thiolcarbamate are added to 767 ml of the above aqueous suspension concentrate, containing 330 g of 1-phenyl-4-amino-5-chloro-pyridaz-6-one; the mixture is then made up to 1,000 ml with distilled water. On vigorous stirring, a completely homogeneous mixture is obtained. With a 2% strength solution of this mixture, only 0.08 ml of sediment has settled out after more than 6 hours, which indicates that the suspendibility of the solid pyridazone is in no way adversely affected by the liquid thiolcarbamate.

The stability does not alter on storing the concentrate for 3 months at $-5°$ C., room temperature, 30° C., 40° C. or 50° C. The suspendibility of the pyridazone remains constant and the liquid thiolcarbamate does not separate out from the aqueous dispersion.

(b) 6 liter portions of the aqueous suspension concentrate described under (a), which contains 430 g of 1-phenyl-4-amino-5-chloro-pyridaz-6-one per liter as the active ingredient, are diluted as follows:

with 50 l of water to give a 10.7% strength spray liquor,
with 100 l of water to give a 5.6% strength spray liquor,
with 200 l of water to give a 2.9% strength spray liquor,
with 300 l of water to give a 1.96% strength spray liquor,
with 400 l of water to give a 1.47% strength spray liquor,
with 500 l of water to give a 1.18% strength spray liquor,
with 600 l of water to give a 0.99% strength spray liquor.

1.2 kg of 2,3-dichloroallyl N,N-diisopropyl-thiolcarbamate are added to each of these aqueous spray liquors, whilst stirring. After from 3 to 5 minutes, a pronounced oily sediment separates out from the spray liquors.

EXAMPLE 2

(a) 756 ml of the aqueous suspension concentrate described in Example 1, containing 325 g of 1-phenyl-4-amino-5-chloro-pyridaz-6-one, 200 g of 2,3,3-trichloroallyl N,N-diisopropyl-thiolcarbamate and 30.2 ml of xylene are mixed and made up to 1,000 ml with distilled water. Thorough stirring gives a formulation which is stable at from −5° C. to +50° C.

(b) 6 liter portions of the aqueous suspension concentrate described under (a), which contains 430 g of 1-phenyl-4-amino-5-chloro-pyridaz-6-one per liter, are diluted as follows:

with 50 l of water to give a 10.7% strength spray liquor,
with 100 l of water to give a 5.6% strength spray liquor,
with 200 l of water to give a 2.9% strength spray liquor,
with 300 l of water to give a 1.96% strength spray liquor,
with 400 l of water to give a 1.47% strength spray liquor,
with 500 l of water to give a 1.18% strength spray liquor,
with 600 l of water to give a 0.99% strength spray liquor.

1.55 kg of 2,3,3-trichloroallyl N,N-diisopropyl-thiolcarbamate together with 234 ml of xylene are added to each of these aqueous spray liquors, whilst stirring. After from 3 to 5 minutes, a pronounced oily sediment separates out from the spray liquors.

EXAMPLE 3

(a) 333 g of ethyl N-ethyl-N-cyclohexyl-thiolcarbamate and sufficient distilled water to give a total volume of 1,000 ml are added to 672 ml of the aqueous suspension concentrate described in Example 1, containing 289 g of 1-phenyl-4-amino-5-chloro-pyridaz-6-one. The components are then mixed by thorough stirring.

A stable formulation is obtained, which in respect of its properties and shelf life is similar to the herbicide described in Example 1(a).

(b) 6 liter portions of the aqueous suspension concentrate described under (a), which contains 430 g of 1-phenyl-4-amino-5-chloro-pyridaz-6-one per liter, are diluted as follows:

with 50 l of water to give a 10.7% strength spray liquor,
with 100 l of water to give a 5.6% strength spray liquor,
with 200 l of water to give a 2.9% strength spray liquor,
with 300 l of water to give a 1.96% strength spray liquor,
with 400 l of water to give a 1.47% strength spray liquor,
with 500 l of water to give a 1.18% strength spray liquor,
with 600 l of water to give a 0.99% strength spray liquor.

1.8 kg of ethyl N-ethyl-N-cyclohexyl-thiolcarbamate are added to each of these aqueous spray liquors, whilst stirring. After from 3 to 5 minutes, the spray liquors exhibit a pronounced oily sediment.

EXAMPLE 4

364 g of ethyl N-ethyl-N-cyclohexyl-thiolcarbamate and sufficient distilled water to give a total volume of 1,000 ml are added to 549 ml of the aqueous suspension concentrate described in Example 1, containing 236 g of 1-phenyl-4-amino-5-chloro-pyridaz-6-one. The components are then mixed by thorough stirring.

A stable formulation is obtained, which in respect of its properties and shelf life is similar to the herbicide described in Example 1(a).

EXAMPLE 5

187.5 g of 2-ethyl-6-methyl-N-ethyl-N-(1-methyl-2-methoxyethyl)-chloroacetanilide and sufficient distilled water to give a total volume of 1,000 ml are added to 756 ml of the aqueous suspension concentrate described in Example 1, containing 325 g of 1-phenyl-4-amino-5-chloro-pyridaz-6-one. The components are then mixed by thorough stirring.

A stable formulation is obtained, which in respect of its properties and shelf life is similar to the herbicide described in Example 1(a).

EXAMPLE 6

333 g of 2-ethyl-6-methyl-N-(1-methyl-2-methoxyethyl)-chloroacetanilide and sufficient distilled water to give a total volume of 1,000 ml are added to 505 ml of the aqueous suspension concentrate described in Example 1, containing 216 g of 1-phenyl-4-amino-5-chloro-pyridaz-6-one. The components are then mixed by thorough stirring.

A stable formulation is obtained, which in respect of its properties and shelf life is similar to the herbicide described in Example 1(a).

EXAMPLE 7

(a) 214 g of 2,6-dinitro-3,4-dimethyl-N-(1-ethyl-n-propyl)-aniline in 100 ml of xylene are added to 498 ml of the aqueous suspension concentrate described in Example 1, containing 214 g of 1-phenyl-4-amino-5-chloro-pyridaz-6-one, and the mixture is made up to 1,000 ml with distilled water. The components are mixed by thorough stirring. A stable formulation is obtained, which in respect of its properties and shelf life is similar to the herbicide described in Example 1(a).

(b) 6 liter portions of the aqueous suspension concentrate described under (a), which contains 430 g of 1-phenyl-4-amino-5-chloro-pyridaz-6-one per liter, are diluted as follows:

with 50 l of water to give a 10.7% strength spray liquor,
with 100 l of water to give a 5.6% strength spray liquor,
with 200 l of water to give a 2.9% strength spray liquor,
with 300 l of water to give a 1.96% strength spray liquor,
with 400 l of water to give a 1.47% strength spray liquor,
with 500 l of water to give a 1.18% strength spray liquor,
with 600 l of water to give a 0.99% strength spray liquor.

1.55 kg of 2,6-dinitro-3,4-dimethyl-N-(1-ethyl-n-propyl)-aniline together with 724 ml of xylene are added to each of these aqueous spray liquors, whilst stirring. After from 3 to 5 minutes, a pronounced granular sediment and crystals of the active ingredient form in the spray liquors.

We claim:

1. A herbicide comprising a stable aqueous suspension containing from 20 to 50 percent by weight of 1-phenyl-4-amino-5-chloro-pyridaz-6-one or 1-phenyl-4-amino-5-bromo-pyridaz-6-one, from 2 to 10 percent by weight of dispersant, from 0.5 to 5 percent by weight of silica and from 0.5 to 5 percent by weight of a block polymer of propylene glycol, propylene oxide and ethylene oxide, which additionally contains a thiolcarbamate of the formula I

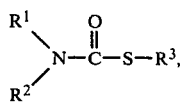

where $R^1$ is alkyl of up to 4 carbon atoms, $R^2$ is alkyl of up to 4 carbon atoms or cyclohexyl and $R^3$ is alkyl of up to 4 carbon atoms, 2,3-dichloroallyl or 2,3,3-trichloroallyl, or a chloroacetanilide of the formula II

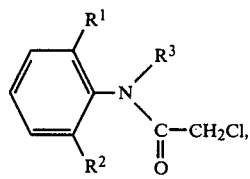

where $R^1$ and $R^2$ are methyl or ethyl and $R^3$ is alkyl of up to 3 carbon atoms or alkoxyalkyl of up to 4 carbon atoms, or a 2,6-dinitroaniline of the formula III

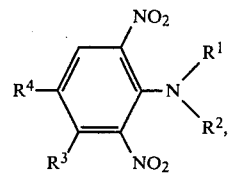

where
$R^1$ is hydrogen or alkyl of up to 5 carbon atoms,
$R^2$ is alkyl of up to 5 carbon atoms and
$R^3$ and $R^4$ are unsubstituted or halogen-substituted alkyl of up to 2 carbon atoms,
the weight ratio of pyridazone to thiolcarbamate, chloroacetanilide or dinitroaniline being from 4:1 to 1:2.

2. A herbicide as claimed in claim 1, which additionally contains an antifreeze.

3. A herbicide as claimed in claim 1, which contains a normally solid thiolcarbamate of the formula I or a chloroacetanilide of the formula II or a 2,6-dinitroaniline of the formula III and additionally contains from 1 to 5% by volume of an alkylbenzene.

4. A herbicide as claimed in claim 1, wherein the thiolcarbamate of the formula I is 2,3-dichloroallyl N,N-diisopropylthiolcarbamate.

5. A process for the preparation of a stable aqueous herbicide suspension in the form of a spray liquor which consists essentially of mixing from 20 to 50% by weight of 1-phenyl-4-amino-5-chloro-pyridaz-6-one or 1-phenyl-4-amino-5-bromo-pyridaz-6-one, from 2 to 10% by weight of a dispersant, from 0.5 to 5% by weight of silica and from 0.5 to 5% by weight of a block polymer of propylene glycol, propylene oxide and ethylene oxide with a thiolcarbamate of the formula I of claim 1 or a chloroacetanilide of the formula II of claim 1 or a 2,6-dinitroaniline of the formula III of claim 1, the weight ratio of pyridazone to thiolcarbamate, chloroacetanilide or dinitroaniline being from 4:1 to 1:2, and thereafter adding to the suspension from 50 to 600 liters of water per 5 to 10 liters of the suspension to form the spray liquor.

* * * * *